United States Patent

Buerstinghaus et al.

Patent Number: 5,185,359
Date of Patent: Feb. 9, 1993

[54] N-PHENOXPHENYLOXYMETHYL SUBSTITUTED AZOLES AND METHOD FOR CONTROLLING PESTS THEREWITH

[75] Inventors: Rainer Buerstinghaus, Telgte; Hans-Juergen Neubauer, Mannheim; Peter Hofmeister, Neustadt; Christoph Kuenast, Otterstadt; Joachim Leyendecker, Mannheim; Uwe Kardorff, Frankenthal, all of Fed. Rep. of Germany

[73] Assignee: BASF Aktiengesellschaft, Ludwigshafen, Fed. Rep. of Germany

[21] Appl. No.: 850,953

[22] Filed: Mar. 11, 1992

Related U.S. Application Data

[62] Division of Ser. No. 516,925, Apr. 30, 1990, Pat. No. 5,116,860, which is a division of Ser. No. 184,804, Apr. 22, 1988, Pat. No. 4,943,585.

Foreign Application Priority Data

May 2, 1987 [DE] Fed. Rep. of Germany ....... 3714709
Jan. 23, 1988 [DE] Fed. Rep. of Germany ....... 3801919

[51] Int. Cl.⁵ .................. A01N 43/56; C07D 231/36; C07D 231/34; C07D 231/18
[52] U.S. Cl. ..................... 514/407; 514/406; 548/376.1; 548/367.1; 548/370.4
[58] Field of Search ............... 548/375, 376, 377, 378; 514/406, 407

References Cited

U.S. PATENT DOCUMENTS 5,013,847   5/1991   Leyendecker et al. ............. 548/378

Primary Examiner—Patricia L. Morris
Attorney, Agent, or Firm—Oblon, Spivak, McClelland, Maier & Neustadt

[57] ABSTRACT

N-substituted azoles of the formula I

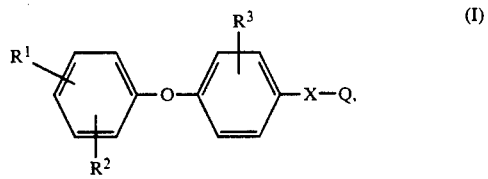

where
$R^1$, $R^2$, $R^3$ are each hydrogen, halogen, $C_1$–$C_8$-alkyl, $C_1$–$C_8$-alkoxy, $C_1$–$C_4$-haloalkyl, $C_1$–$C_4$-haloalkoxy, $C_3$–$C_{10}$-cycloalkyl, nitro or cyano, Q is an unsubstituted or substituted azole group of the formulae IIa–IIf $R^4$ to $R^{15}$ denoting hydrogen, halogen, $C_1$–$C_8$-alkyl, $C_1$–$C_4$-haloalkyl, $C_1$–$C_4$-alkoxy, $C_3$–$C_{10}$-cycloalkyl or aryl which is unsubstituted or mono-, di- or trisubstituted by halogen, $C_1$–$C_8$-alkyl, $C_1$–$C_8$-alkoxy, $C_1$–$C_4$-haloalkyl or $C_1$–$C_4$-haloalkoxy, and
X is, in the case of the azole group IIa, —CH$_2$— or —O(CH$_2$)$_n$—, n being one of the integers 1, 2 or 3, or, in the case of the azole groups IIb–IIf, —OCH$_2$—, pesticides containing compounds I as active ingredients, and a process for combating pests.

4 Claims, No Drawings

N-PHENOXPHENYLOXYMETHYL SUBSTITUTED AZOLES AND METHOD FOR CONTROLLING PESTS THEREWITH

This is a division of application Ser. No. 07/516,925, filed on Apr. 30, 1990, now U.S. Pat. No. 5,116,860, which is a division of Ser. No. 07/184,804, filed Apr. 22, 1988, now U.S. Pat. No. 4,943,585.

The present invention relates to novel N-substituted azoles of the general formula:

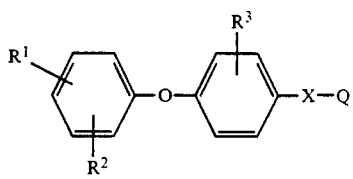

where $R^1$, $R^2$ and $R^3$ are each hydrogen, halogen, $C_1$-$C_8$-alkyl, $C_1$-$C_8$-alkoxy, $C_1$-$C_4$-haloalkyl, $C_1$-$C_4$-haloalkoxy, $C_3$-$C_{10}$-cycloalkyl, nitro or cyano, Q is an unsubstituted or substituted azolyl radical of the formulae IIa-IIe

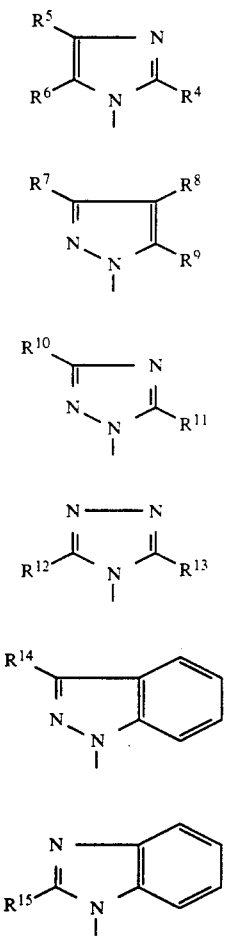

where $R^4$ to $R^{15}$ are each hydrogen, halogen, $C_1$-$C_8$-alkyl, $C_1$-$C_4$-haloalkyl, $C_1$-$C_4$-alkoxy, $C_3$-$C_{10}$-cycloalkyl or aryl which is unsubstituted or monosubstituted to trisubstituted by halogen, $C_1$-$C_8$-alkyl, $C_1$-$C_8$-alkoxy, $C_1$-$C_4$-haloalkyl or $C_1$-$C_4$-haloalkoxy, and X is —$CH_2$— or —$O(CH_2)_n$—, where n is 1, 2 or 3, in the case of the azolyl radical IIa and is —$OCH_2$— in the case of the azolyl radicals IIb–IIf.

The present invention furthermore relates to pesticides which contain the compounds I as active ingredients, and a method for controlling pests.

EP-A-132 606 discloses N-substituted azoles as insecticidal and acaricidal active ingredients. However, the action of these compounds is unsatisfactory.

It is an object of the present invention to provide novel N-substituted azoles I having an improved action.

We have found that this object is achieved by the novel N-substituted azoles I defined at the outset. We have also found that the compounds I are very suitable for controlling pests.

The compounds I are obtainable by the following methods:

a) For the preparation of the compounds I in which X is —$CH_2$—, a p-phenoxybenzyl compound III is reacted with an anion of an imidazole IV in accordance with the following equation:

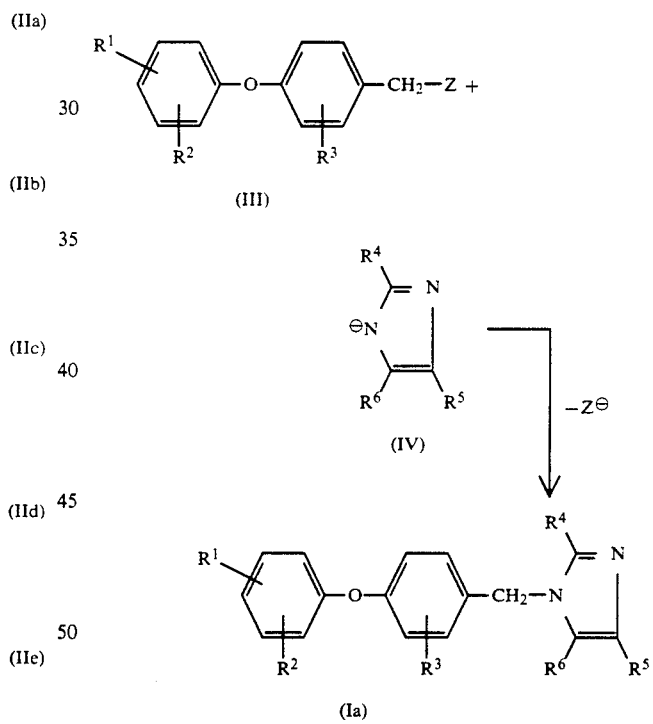

Some of the p-phenoxybenzyl compounds III are known from the literature (for example from GB-A-1 140 748, DE-A-24 18 572 and EP-A-132 606); those which are unknown can be prepared in a conventional manner.

The anions of the imidazoles IV can be generated from imidazoles IVa which are known from the literature or are commercially available, by a conventional method, in the form of the corresponding salts, such as the sodium or potassium salt.

The compounds Ia can also be obtained by reacting III with an imidazole IVa

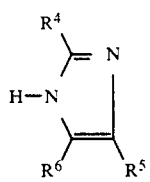

(IVa)

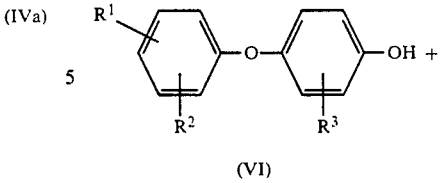

in the presence of a base. Not less than equivalent amounts of a base are usually added to III and/or IVa, although these may also be used in excess or, as the case may be, even as a solvent. Examples of suitable bases are alcoholates of alkali metals, such as sodium methylate, sodium ethylate or potassium tert-butylate, alkali metal or alkaline earth metal hydrides, such as sodium hydride, potassium hydride or calcium hydride, alkali metal carbonates, such as sodium carbonate or potassium carbonate, aliphatic amines, such as dimethylamine, triethylamine or diisopropylamine, heterocyclic amines, such as piperidine, piperazine or pyrrolidine, aromatic amines, such as pyridine or pyrrole, and, if required, also alkyllithium compounds, such as n-butyllithium.

b) For the preparation of the compounds I in which X is —O(CH$_2$)$_2$— or —O(CH$_2$)$_3$—, a p-phenoxyphenoxy compound V is reacted with an anion of an imidazole IV in accordance with the following equation:

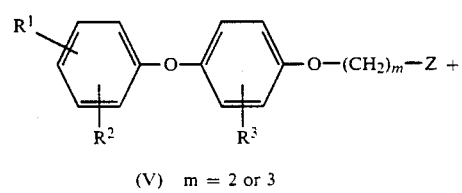

(V) m = 2 or 3

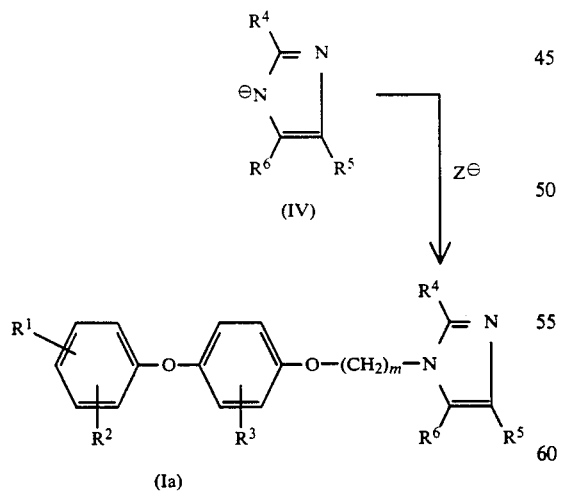

(Ia)

c1) For the preparation of the compounds I in which X is —OCH$_2$—, a p-phenoxyphenol VI is reacted with an N-methylazole VII in the presence of a base at from −20° to 250° C., preferably from 20° to 120° C., in accordance with the following equation:

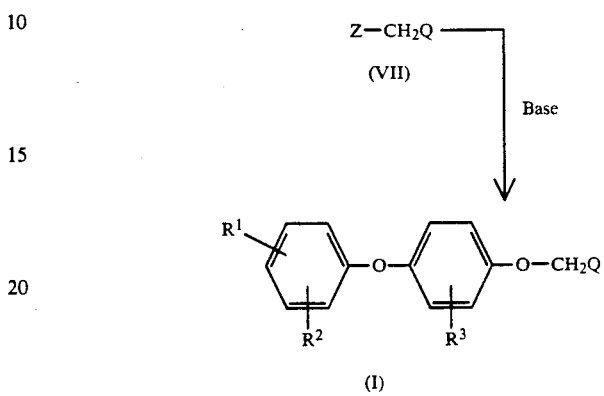

Some of the p-phenoxyphenols VI are disclosed in Houben-Weyl, Vol. VI, 3, Methoden der org. Chemie, Thieme Verlag, 1965, 585 et seq.; those which are not known can be prepared by the methods described there.

Some of the N-methylazoles VII are disclosed in Heterocycles 24 (1986), 2233; those which are not known can be prepared by the method described there, in accordance with the following equation:

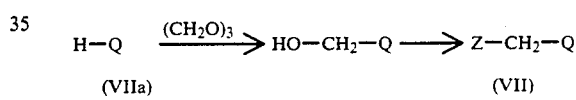

c2) For the preparation of the compounds I in which X is —OCH$_2$—, a phenolate anion of VI is reacted with an N-methylazole VII at from −20° to 120° C., preferably from −20° to 80° C., in accordance with the following equation:

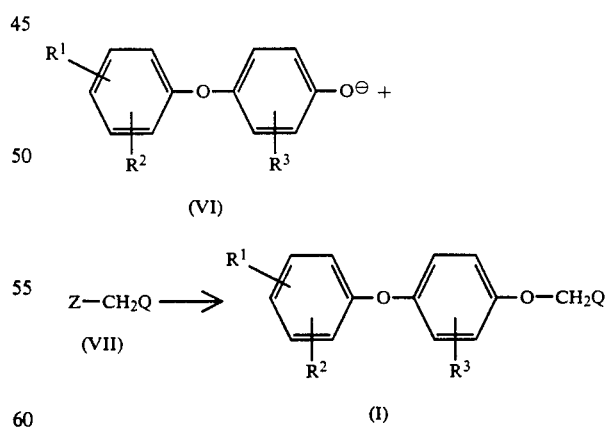

The p-phenoxyphenolate anions VI are known in the form of their metal salts, such as the sodium or potassium salt, or can be generated from the p-phenoxyphenols by reaction with conventional metallization reagents, such as sodium methylate, sodium ethylate, potassium tert-butylate, sodium hydride, potassium hydride or butyllithium.

In all four embodiments, Z is a leaving group, for example a sulfonic acid radical or a halogen. Preferred sulfonic acid radicals are methanesulfonyl, trifluoromethanesulfonyl and p-toluenesulfonyl, and preferred halogens are chlorine and bromine, chlorine being particularly preferred.

The reactions of the particular anions of the metal salts in cases a), b), c1) and c2) are advantageously carried out in a solvent or diluent. For example, aliphatic hydrocarbons, such as n-pentane, n-hexane, a mixture of hexaneisomers, petroleum ether, cyclohexane or heptane, aromatic hydrocarbons, such as benzene, toluene, the xylenes and their isomer mixtures, gasoline, chlorohydrocarbons, such as methylene chloride, chloroform, carbon tetrachloride or 1,2-dichloromethane, chlorinated aromatics, such as chlorobenzene or 1-chloronaphthalene, ethers, such as diethyl ether, di-n-butyl ether, methyl tert-butyl ether, tetrahydrofuran or dioxane, ketones, such as acetone, methyl ethyl ketone or methyl isopropyl ketone, nitriles, such as acetonitrile or propionitrile, and aprotic dipolar solvents, such as dimethylformamide, dimethyl sulfoxide or pyridine, are suitable for this purpose. Mixtures of these substances can also be used as solvents or diluents.

For the preparation of the novel compounds I by the methods described above, the starting materials are usually used in a stoichiometric ratio. However, an excess of one or other of the starting materials may be very advantageous in specific cases.

The reactions usually take place at an adequate rate above $-30°$ C. In general, $100°$ C. must not be exceeded. Since they take place with evolution of heat in some cases, it may be advantageous to provide a means of cooling.

The reaction mixtures are worked up in a conventional manner, for example by the addition of water, separation of the phases and column chromatography. Some of the novel compounds of the formula I are obtained in the form of a colorless or pale brownish, viscous oil, which can be freed from the last volatile components by prolonged heating at moderately elevated temperatures under reduced pressure and can be purified in this manner. If the compounds of the formula I are obtained in crystalline form, they may be purified by recrystallization.

The substituents in formula I have the following specific meanings: $R^1$ is hydrogen, halogen, preferably fluorine, chlorine or bromine, particularly preferably fluorine or chlorine in the meta-position, straight-chain or branched $C_1$-$C_8$-alkyl, preferably straight-chain or branched $C_1$-$C_6$-alkyl, particularly preferably straight-chain or branched $C_1$-$C_4$-alkyl in the meta-position, such as m-methyl, m-ethyl, m-(n-propyl), m-isopropyl, m-(n-butyl), m-isobutyl, m-(sec-butyl) and m-(tert-butyl), straight-chain or branched $C_1$-$C_8$-alkoxy, preferably straight-chain or branched $C_1$-$C_4$-alkoxy, particularly preferably $C_1$- or $C_2$-alkoxy in the meta-position, such as m-methoxy or m-ethoxy, straight-chain or branched $C_1$-$C_4$-haloalkyl, preferably $C_1$- or $C_2$-fluoro- or chloroalkyl, particularly preferably m-trifluoromethyl or m-trichloromethyl, straight-chain or branched $C_1$-$C_4$-haloalkoxy, preferably $C_1$- or $C_2$-fluoro- or chloroalkoxy, particularly preferably m-trifluoromethoxy or m-trichloromethoxy, $C_3$-$C_{10}$-cycloalkyl, preferably $C_3$-$C_6$-cycloalkyl, particularly preferably m-cyclopropyl, m-cyclobutyl, m-cyclopentyl or m-cyclohexyl, nitro or cyano, $R^2$ and $R^3$ independently of one another are each hydrogen, halogen, preferably fluorine or chlorine, straight-chain or branched $C_1$-$C_8$-alkyl, preferably straight-chain or branched $C_1$-$C_4$-alkyl, particularly preferably $C_1$- or $C_2$-alkyl, such as methyl or ethyl, straight-chain or branched $C_1$-$C_8$-alkoxy, preferably straight-chain or branched $C_1$-$C_4$-alkoxy, particularly preferably $C_1$- or $C_2$-alkoxy, such as methoxy or ethoxy, straight-chain or branched $C_1$-$C_4$-haloalkyl, preferably $C_1$- or $C_2$-fluoro- or chloroalkyl, particularly preferably trifluoromethyl or trichloromethyl, straight-chain or branched $C_1$-$C_4$-haloalkoxy, preferably $C_1$- or $C_2$-fluoro- or chloroalkoxy, particularly preferably trifluoromethoxy or trichloromethoxy, $C_3$-$C_{10}$-cycloalkyl, preferably $C_3$-$C_6$-cycloalkyl, such as cyclopropyl, cyclobutyl, cyclopentyl or cyclohexyl, particularly preferably cyclopropyl, nitro or cyano, $R^4$ to $R^{15}$ independently of one another are each hydrogen, halogen, preferably fluorine or chlorine, straight-chain or branched $C_1$-$C_8$-alkyl, preferably straight-chain or branched $C_1$-$C_4$-alkyl, particularly preferably $C_1$- or $C_2$-alkyl, such as methyl or ethyl, straight-chain or branched $C_1$-$C_4$-haloalkyl, preferably $C_1$- or $C_2$-fluoro, chloroalkyl, particularly preferably trifluoromethyl or trichloromethyl, straight-chain or branched $C_1$-$C_8$-alkoxy, preferably straight-chain or branched $C_1$-$C_4$-alkoxy, particularly preferably $C_1$- or $C_2$-alkoxy, such as methoxy or ethoxy, $C_3$-$C_{10}$-cycloalkyl, preferably $C_3$-$C_3$-cycloalkyl, such as cyclopropyl, cyclobutyl, cyclopentyl or cyclohexyl, particularly preferably cyclopropyl, aryl, preferably phenyl, 1-naphthyl or 2-naphthyl, particularly preferably phenyl, aryl which is monosubstituted to trisubstituted by halogen, preferably phenyl which is monosubstituted by fluorine or chlorine, such as 2-fluorophenyl, 3-fluorophenyl, 4-fluorophenyl, 2-chlorophenyl, 3-chlorophenyl or 4-chlorophenyl, aryl which is monosubstituted to trisubstituted by straight-chain or branched $C_1$-$C_8$-alkyl, preferably phenyl which is monosubstituted by straight-chain or branched $C_1$-$C_4$-alkyl, particularly preferably phenyl which is monosubstituted by $C_1$- or $C_2$-alkyl, such as 4-methylphenyl or 4-ethylphenyl, aryl which is monosubstituted to trisubstituted by straight-chain or branched $C_1$-$C_8$-alkoxy, preferably phenyl which is monosubstituted by straight-chain or branched $C_1$-$C_4$-alkoxy, particularly preferably phenyl which is monosubstituted by $C_1$- or $C_2$-alkoxy, such as 4-methoxyphenyl or 4-ethoxyphenyl, aryl which is monosubstituted to trisubstituted by straight-chain or branched $C_1$-$C_4$-haloalkyl, preferably phenyl which is monosubstituted by $C_1$- or $C_2$-fluoro- or chloroalkyl, particularly preferably phenyl which is monosubstituted by trifluoromethyl or trichloromethyl, such as 4-trifluoromethylphenyl or 4-trichloromethylphenyl, aryl which is monosubstituted to trisubstituted by straight-chain or branched $C_1$-$C_4$-haloalkoxy, preferably phenyl which is monosubstituted by $C_1$- or $C_2$-fluoro- or chloroalkoxy, particularly preferably phenyl which is monosubstituted by trifluoromethoxy or trichloromethoxy, such as 4-trifluoromethoxyphenyl or 4-trichloromethoxy, such and X is $-CH_2-$, $-OCH_2-$, $-O(CH_2)_2-$ or $-O(CH_2)_3-$.

In contrast to most of the active ingredients known to date, which act as contact or ingested poisons and kill, incapacitate or repel the animals, most of the compounds of the formula I interfere with the development of the animal organism. In the case of insects, for example, the transformation to the imago, the laying of viable eggs and the development of normal laid eggs are disturbed and the sequence of generations thus interrupted. The active ingredients according to the invention are virtually completely non-toxic for vertebrates. Moreover, most the compounds of the formula I are readily degraded to substances which occur in nature and are further decomposed by microorganisms.

The N-substituted azoles of the general formula I are suitable for effectively combating pests from the class consisting of insects, Arachnida and nematodes. The compounds may be used as pesticides for protecting crops and in the hygiene, stores protection and veterinary sectors.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha, Pieris brassicae,* and *Aporia crataegi;* examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are root-knot nematodes, e.g., *Meloidogyne icognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, in the form of formulations or application forms prepared therefrom, e.g., as directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions, the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 5 parts by weight of compound no. 1 is intimately mixed with 95 parts by weight of particulate kaolin. A dust is obtained containing 5% by weight of the active ingredient.

II. 30 parts by weight of compound no. 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 7 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 9 is dissolved is a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 41 is well mixed with 3 parts by weight of the sodium salt of diisobutylnaphthalene-alpha-sulfonic acid 10 parts by weight of the sodium salt of a lignin-sulfonic acid obtained from a sulfite waste liquor, and 7 parts by weight of powdered silica gel, and triturated in a hammer mill.

The active ingredient concentrations in the finished formulations may vary over a wide range. Generally, they are from 0.0001 to 10, and preferably from 0.01 to 1, %. The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.001 to 10, and preferably from 0.1 to 1, kg/ha.

There may be added to the active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene 1,2-dichloropropane, 1,2-dibromethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propion aldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethylphosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphoro dithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimiidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5[4H]-only-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]phosphorothioate, O,O-diethyl-O-[2-(diethylamino)-6-methyl-4-pyrimidinyl]-thionophosphate, O,O-dimethyl-S-(4-oxo-1,2,3-benzotriazin-3[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropanecarboxylate, (s)-alpha-cyano-3-phenoxybenzyl-cis(1R,3R)-2,2-dimethyl-3-(2,2-dibromovinyl)-cyclopropanecarboxylate, 3,4,5,6-tetrahydrophthalimidoethyl-DL-cis,trans-chrysanthemate, 2-methyl-5-(2-propynyl)-3-furylmethyl-chrysanthemate, and alpha-cyano-3-phenoxybenzyl-alpha-isopropyl-4-chlorophenylacetate.

MANUFACTURING EXAMPLES

Example 1

N-[(p-phenoxyphenoxy)-methyl]-4,5-dichloroimidazole (compound 1)

94 g of 1-hydroxymethyl-4,5-dichloroimidazole is dissolved in 550 ml of carbon tetrachloride. 1 ml of dimethylformamide is added, and 100.5 g of thionyl chloride is dripped in while stirring. The mixture is refluxed until no more gas evolves, after which the solvent is removed under reduced pressure and 750 ml of methylene chloride and 250 ml of water are added to the residue. While the mixture is stirred thoroughly, its pH is brought to 7.5 with 5% strength aqueous sodium hydroxide solution. The organic phase is then separated, washed with water and dried over sodium sulfate. The residue remaining after removal of the solvent is distilled at 92° to 95° C./0.1 mbar. There is obtained 80.5 g (77%) of 1-chloromethyl-4,5-dichloroimidazole; m.p.: 40°–41° C.

9.3 g of 4-phenoxyphenol is dissolved in 60 ml of anhydrous dimethylformamide. 1.58 g of 80% strength sodium hydride is added, and the mixture is heated at 60° C. until no more hydrogen evolves (about 1 hour). A solution of 9.28 g of N-(1-chloromethyl)-4,5-dichloroimidazole in 30 ml of dimethylformamide is then dripped in. The mixture is stirred overnight at room temperature, after which it is poured into 500 ml of water, followed by extraction three times with methyl tert-butyl ether. The combined organic phases are washed three times with water, dried over sodium sulfate, and freed from solvent under reduced pressure. The solid residue is recrystallized from n-pentane/ether (6:1) to give N-[(p-phenoxyphenoxy)-methyl]-4,5-dichloroimidazole, m.p.: 82°–83° C.

$C_{16}H_{12}Cl_2N_2O_2$ (335): calc.: C 57.4, H 3.6, N 8.4. found: C 57.7, H 3.7, N 8.3.

Infrared absorptions ($cm^{-1}$): 1478, 1403, 1235, 1209, 1047, 854.

Example 2

N-[p-(3-chlorophenoxy)-benzyl]-4,5-dimethylimidazole (compound 2)

While stirring thoroughly, 1.91 g of 80% strength sodium hydride is introduced into a solution of 6.04 g of 4,5-dimethylimidazole in 80 ml of tetrahydrofuran. Upon completion of the exothermic reaction, the mixture is kept for 3 hours at 60° C., and then cooled. A solution of 17.85 g of p-(3-chlorophenoxy)-benzyl bromide in 20 ml of tetrahydrofuran is then added. The reaction batch is stirred for 12 hours at 20° C., then poured into about 750 ml of ice water and extracted by shaking with methyl tert-butyl ether. The extract is washed twice with 5% strength aqueous sodium hydroxide solution and twice with water. After the extract has been dried over sodium sulfate, the solvent is removed under reduced pressure and the residue is chromatographed over silica gel 60 with acetone/ethyl acetate (2:1). There is obtained 12.1 g (65%) of N-[p-(3-chlorophenoxy)-benzyl]-4,5-dimethylimidazole as a resin-like liquid which slowly crystallizes on standing.

$C_{18}H_{17}ClN_2O$ (312.5): calc.: C 69.1, H 5.5, N 9.0. found: C 69.1, H 5.5, N 8.9.

Infrared absorptions ($cm^{-1}$): 1505, 1474, 1306, 1226, 901.

Example 3

N-[(p-phenoxyphenoxy)-ethyl]-4,5-dichloroimidazole (compound 3)

23.0 g of 2-(4-phenoxyphenoxy)-ethanol and 22.9 g of p-toluenesulfonyl chloride are dissolved in 100 ml of methylene chloride; 18.96 g of pyridine is dripped in at from 10° to 15° C. The mixture is stirred for 30 minutes at room temperature and for 4 hours under reflux. The solvent is then removed under reduced pressure, and the residue is dissolved in 150 ml of pyridine and poured into 600 ml of ice water. The solid which precipitates is filtered off, dried and recrystallized from cyclohexane/methyl tert-butyl ether (5:1). There is obtained 28.2 g (73%) of 2-[(p-phenoxyphenoxy)-ethyl] p-toluenesulfonate; m.p.: 53°-55° C.

A mixture of 8.43 g of 4,5-dichloroimidazole, 80 ml of dimethylformamide and 1.83 g of sodium hydride is heated, with stirring, for 3 hours at 60° C. Subsequently, a solution of 23.04 g of 2-[(p-phenoxyphenoxy)-ethyl] p-toluenesulfonate in 40 ml of dimethylformamide is dripped in. The mixture is heated for 12 hours at 100° C., cooled, poured into 50 ml of ice water, and extracted several times with ethyl acetate, and the combined extracts are washed first with 5% strength aqueous sodium hydroxide solution and then with water. Drying over sodium sulfate, removal of the solvent under reduced pressure and recrystallization from methyl tert-butyl ether gives 16.9 g (81%) of N-[(p-phenoxyphenoxy)-ethyl]-4,5-dichloroimidazole; m.p.: 89°-91° C.

$C_{17}Cl_2N_2O_2$ (349): calc.: C 58.5, H 4.0, N 8.0. found: C 58.2, H 4.1, N 7.9.

Infrared absorptions (cm$^{-1}$): 1489, 1462, 1255, 1214, 1190, 1063, 845.

Example 4

N-[(p-phenoxyphenoxy)-n-propyl]-imidazole
(compound 4)

24.4 g of 3-(4-phenoxyphenoxy)-propan-1-ol is added in portions to a solution of 9.5 g of phosphorus tribromide in 65 ml of tetrachloromethane. When the exothermic reaction has subsided, the mixture is heated for 4 hours at 40° C. After the mixture has cooled, the solvent is removed under reduced pressure, the residue is dissolved in 300 ml of methyl tert-butyl ether, and the organic phase is washed thoroughly with water and dried over sodium sulfate. The crude product remaining after removal of the solvent is purified by silica gel filtration with toluene/methyl tert-butyl ether (2:1). There is obtained 20.8 g (67%) of 3-(p-phenoxyphenoxy)-1-bromopropane; m.p.: 54°-55° C.

1.98 g of 80% strength sodium hydride is added in portions to a solution of 4.25 g of imidazole in 70 ml of dimethylformamide. Upon completion of hydrogen evolution the mixture is stirred for a further 3 hours at 60° C., after which a solution of 18.42 g of 3-[4-(phenoxy)-phenoxy]-1-bromopropane in 40 ml of dimethylformamide is added. The mixture is heated for 8 hours at 80° C. and then poured into 2.5 liters of ice water. The solid which separates out is filtered off in a desiccator, dried over calcium chloride and purified by filtration over silica gel. There is obtained 14.5 g (82%) of N-[(p-phenoxyphenoxy)-n-propyl]-imidazole; m.p.: 54.5°-55.5° C.

$C_{18}H_{18}N_2O_2$ (294): calc.: C 73.4, H 6.2, N 9.5. found: C 73.1, H 6.3, N 9.4.

Infrared absorptions (cm$^{-1}$): 1489, 1224, 1196, 1166, 1075, 849.

EXAMPLE 5

1-{[p-(3-methyl)-phenoxyphenoxy]-methyl}-1,2,4-triazole (compound no. 135)

At room temperature (about 20° C.), 7.7 g of 1-chloromethyl-1,2,4-triazole hydrochloride is added to 10 g of p-(3-methylphenoxy)-phenol and 20.7 g of potassium carbonate in 60 ml of anhydrous dimethylformamide. The mixture is then stirred for 6 hours at 70° C. and overnight at room temperature (about 20° C.). The mixture is then poured into 300 ml of water, followed by extraction three times with methyl tert-butyl ether. The combined organic phases are washed three times with water, dried over sodium sulfate and concentrated. The residue is purified by chromatography over silica gel using toluene/methyl tert-butyl ether (2:1) as eluant. There is obtained 5.1 g of 1-{[p-(3-methyl)-phenoxyphenoxy]-methyl}-1,2,4-triazole; m.p.: 52°-54° C.

EXAMPLE 6

2-Chloro-1-[(p-phenoxyphenoxy)-methyl]-1,3,4-triazole
(compound no. 177)

5.6 g of p-phenoxyphenol and 4.2 g of potassium carbonate are heated for 1 hour at 70° C. in 50 ml of anhydrous dimethylformamide. Subsequently, 5.6 g of 2-chloro-1-chloromethyl-1,3,4-triazole is added and the mixture stirred for 6 hours at 70° C. and overnight at room temperature (about 20° C.). The mixture is then poured into 500 ml of water and extracted three times with ethyl acetate. The combined organic phases are dried over magnesium sulfate and concentrated. The residue is purified by chromatography over silica gel using n-hexane/ethyl acetate (2:1) as eluant. There is obtained 2.8 g of 2-chloro-1-[(p-phenoxyphenoxy)-methyl]-1,3,4-triazole as an oil.

300 MHz NMR in CDCl$_3$ δ [ppm]: 5.95 (2H), 6.90-7.15 (7H), 7.25-7.38 (2H), 8.15 (1H).

EXAMPLE 7

1-[(p-phenoxyphenoxy)-methyl]-benzimidazole
(compound no. 213)

At room temperature (about 20° C.) and under a nitrogen blanket, 13.95 g of p-phenoxyphenol in 100 ml of anhydrous dimethylformamide is dripped into 6.75 g of 80% strength sodium hydride in 50 ml of anhydrous dimethylformamide. Upon completion of hydrogen evolution, the mixture is stirred for 4 hours at 60° C. At 10° C., 15.22 g of 1-chloromethylbenzimidazole hydrochloride is then added. The mixture is stirred for 8 hours at 120° C. After concentration under reduced pressure, the residue is taken up in ethyl acetate, and washed three times with water and three times with 5% strength aqueous sodium hydroxide solution. The combined organic phases are dried over sodium sulfate and concentrated. The residue is recrystallized from diethyl ether. There is obtained 11.8 g of 1-[(p-phenoxyphenoxy)-methyl]-benzimidazole of m.p. 112° C.

The compounds Ia-If listed in Tables 1 to 6 below may be prepared in accordance with the above directions.

TABLE 1

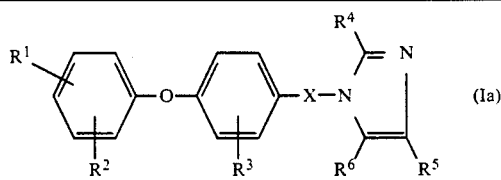

| Compound No. | R¹ | R² | R³ | X | R⁴ | R⁵=R⁶ | Phys. data [IR absorptions (cm⁻¹)] |
|---|---|---|---|---|---|---|---|
| 1 | H | H | H | OCH$_2$ | H | Cl | 1478, 1403, 1235, 1209 |
| 2 | 3-Cl | H | H | CH$_2$ | H | CH$_3$ | 1505, 1474, 1306, 1226 |
| 3 | H | H | H | O(CH$_2$)$_2$ | H | Cl | 1489, 1462, 1255, 1214 |
| 4 | H | H | H | O(CH$_2$)$_3$ | H | H | 1489, 1224, 1196, 1166 |
| 5 | 4-F | H | H | CH$_2$ | H | Cl | 1250, 1212, 1193, 1180 |
| 6 | 4-OCH$_3$ | H | H | CH$_2$ | H | CH$_3$ | 1443, 1228, 1034 |
| 7 | 4-Cl | H | H | CH$_2$ | H | CH$_3$ | 1240, 1167, 1089 |
| 8 | 4-Cl | H | H | CH$_2$ | H | Cl | 1244, 1168, 1098, 1018 |
| 9 | 3-Cl | H | H | CH$_2$ | H | Cl | 1471, 1238, 1169 |
| 10 | H | H | H | CH$_2$ | H | Cl | 1242, 1169, 983 |
| 11 | H | H | H | CH$_2$ | H | CH$_3$ | 1447, 1237, 1167 |
| 12 | 4-NO$_2$ | H | H | CH$_2$ | H | CH$_3$ | 1336, 1248, 1201, 1189 |
| 13 | 4-NO$_2$ | H | H | CH$_2$ | H | Cl | 1338, 1247, 1202, 1167 |
| 14 | 4-F | H | H | CH$_2$ | H | CH$_3$ | 1253, 1213, |
| 15 | 4-C$_2$H$_5$ | H | H | CH$_2$ | H | Cl | 1245, 1170, 982 |
| 16 | 4-OCH$_3$ | H | H | CH$_2$ | H | Cl | 1250, 1169, 1033 |
| 17 | 4-CH$_3$ | H | H | CH$_2$ | H | Cl | 1248, 1172 |
| 18 | 4-CH$_3$ | H | H | CH$_2$ | H | CH$_3$ | 1241, 1171 |
| 19 | 4-C$_2$H$_5$ | H | H | CH$_2$ | H | CH$_3$ | 1447, 1238, 1169 |
| 20 | H | H | H | CH$_2$ | H | Cl | |
| 21 | 3-CF$_3$ | H | H | CH$_2$ | H | Cl | |
| 22 | 3-F | 4-F | H | CH$_2$ | H | Cl | |
| 23 | 4-CF$_3$ | H | H | CH$_2$ | H | Cl | |
| 24 | H | H | H | CH$_2$ | Br | Cl | |
| 25 | H | H | H | CH$_2$ | Cl | Cl | |
| 26 | H | H | H | O(CH$_2$)$_2$ | H | CH$_3$ | 1447, 1254, 1220, 1059 |
| 27 | H | H | H | O(CH$_2$)$_2$ | H | H | 1460, 1231, 1218, 1108 |
| 28 | 3-F | H | H | O(CH$_2$)$_2$ | H | Cl | |
| 29 | 3-Cl | H | H | O(CH$_2$)$_2$ | H | Cl | |
| 30 | 3-CF$_3$ | H | H | O(CH$_2$)$_2$ | H | Cl | |
| 31 | 3-F | 4-F | H | O(CH$_2$)$_2$ | H | Cl | |
| 32 | 4-CF$_3$ | H | H | O(CH$_2$)$_2$ | H | Cl | |
| 33 | 3-CH$_3$ | H | H | O(CH$_2$)$_2$ | H | Cl | |
| 34 | H | H | H | O(CH$_2$)$_2$ | Cl | Cl | |
| 35 | 3-Cl | H | H | O(CH$_2$)$_2$ | Cl | Cl | |
| 36 | H | H | H | O(CH$_2$)$_2$ | Br | Cl | |
| 37 | 3-Cl | H | H | O(CH$_2$)$_2$ | Br | Cl | |
| 38 | 3-F | H | H | O(CH$_2$)$_2$ | Br | Cl | |
| 39 | 3-CF$_3$ | H | H | O(CH$_2$)$_2$ | Br | Cl | |
| 40 | 3-F | 4-F | H | O(CH$_2$)$_2$ | Br | Cl | |
| 41 | H | H | H | O(CH$_2$)$_3$ | H | Cl | 1258, 1250, 1219, 1191 |
| 42 | H | H | H | O(CH$_2$)$_2$ | H | CH$_3$ | 1473, 1220, 1186 |
| 43 | 4-F | H | H | O(CH$_2$)$_2$ | H | Cl | |
| 44 | 4-F | H | H | OCH$_2$ | H | Cl | 1483, 1205, 1116, 1035 |
| 45 | 4-Cl | H | H | OCH$_2$ | H | Cl | 1472, 1240, 1212, 1186 |
| 46 | 3-CF$_3$ | H | H | OCH$_2$ | H | Cl | 1329, 1213, 1185, 1125 |
| 47 | 4-CH$_3$ | H | H | OCH$_2$ | H | Cl | 1501, 1255, 1244, 1203 |
| 48 | 3-F | 4-F | H | OCH$_2$ | H | Cl | 1250, 1225, 1203, 1187 |
| 49 | 4-F | H | H | OCH$_2$ | H | Cl | 1496, 1403, 1236, 1230 |
| 50 | 4-CF$_3$ | H | H | OCH$_2$ | H | Cl | |
| 51 | H | H | H | OCH$_2$ | Br | Cl | |
| 52 | 4-Cl | H | H | OCH$_2$ | Br | Cl | |
| 53 | 3-F | H | H | OCH$_2$ | Br | Cl | |
| 54 | 3-CF$_3$ | H | H | OCH$_2$ | Br | Cl | |
| 55 | 3-CH$_3$ | H | H | OCH$_2$ | Br | Cl | |
| 56 | 4-F | H | H | OCH$_2$ | Br | Cl | |
| 57 | 4-CF$_3$ | H | H | OCH$_2$ | Br | Cl | |
| 58 | 4-Cl | H | H | OCH$_2$ | Br | Cl | |
| 59 | 3-F | 4-F | H | OCH$_2$ | Br | Cl | |
| 60 | H | H | H | OCH$_2$ | Cl | Cl | |
| 61 | 3-Cl | H | H | OCH$_2$ | Cl | Cl | |
| 62 | 3-F | H | H | OCH$_2$ | Cl | Cl | |
| 63 | 3-CF$_3$ | H | H | OCH$_2$ | Cl | Cl | |
| 64 | 4-F | H | H | OCH$_2$ | Cl | Cl | |
| 65 | 4-CF$_3$ | H | H | OCH$_2$ | Cl | Cl | |
| 66 | 4-Cl | H | H | OCH$_2$ | Cl | Cl | |
| 67 | 3-Cl | H | H | O(CH$_2$)$_3$ | H | Cl | |
| 68 | 4-F | H | H | O(CH$_2$)$_3$ | H | Cl | |
| 69 | 4-CF$_3$ | H | H | O(CH$_2$)$_3$ | H | Cl | |
| 70 | 4-CH$_3$ | H | H | O(CH$_2$)$_3$ | H | Cl | |
| 71 | 3-F | 4-F | H | O(CH$_2$)$_3$ | H | Cl | |

TABLE 1-continued

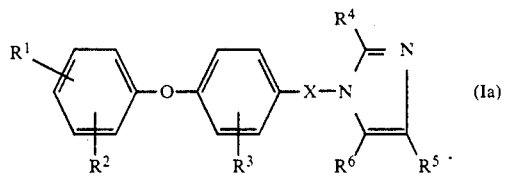

(Ia)

| Compound No. | R¹ | R² | R³ | X | R⁴ | R⁵=R⁶ | Phys. data [IR absorptions (cm⁻¹)] |
|---|---|---|---|---|---|---|---|
| 72 | 4-F | H | H | O(CH₂)₃ | H | Cl | |
| 73 | 4-Cl | H | H | O(CH₂)₃ | H | Cl | |
| 74 | H | H | H | O(CH₂)₃ | Cl | Cl | |
| 75 | H | H | H | O(CH₂)₃ | Br | Cl | |
| 76 | 3-Cl | H | H | O(CH₂)₃ | Cl | Cl | |
| 77 | 3-Cl | H | H | O(CH₂)₃ | Br | Cl | |
| 78 | 3-F | H | H | O(CH₂)₃ | Br | Cl | |
| 79 | 3-F | H | H | O(CH₂)₃ | Cl | Cl | |
| 80 | 3-Br | H | H | OCH₂ | H | Cl | 1490, 1470, 1402, 1237 |
| 81 | 4-Cl | H | H | OCH₂ | H | Cl | 1502, 1489, 1253, 1245 |
| 82 | 4-Br | H | H | OCH₂ | H | Cl | 1486, 1244, 1206, 1183 |
| 83 | 4-CH₃ | H | H | OCH₂ | H | Cl | 1501, 1257, 1245, 1204 |
| 84 | 4-C₂H₅ | H | H | OCH₂ | H | Cl | 1498, 1242, 1206, 1186 |
| 85 | 4-F | H | H | OCH₂ | H | Cl | 1481, 1244, 1221, 1203 |
| 86 | 3-Cl | 4-Cl | H | OCH₂ | H | Cl | 1502, 1468, 1255, 1244 |
| 87 | 4-tert-C₄H₉ | H | H | OCH₂ | H | Cl | 1501, 1481, 1406, 1231 |
| 88 | 4-OCH₃ | H | H | OCH₂ | H | Cl | 1498, 1489, 1405, 1236 |
| 89 | 4-OC₂H₅ | H | H | OCH₂ | H | H | 1498, 1490, 1405, 1239 |
| 90 | H | H | H | OCH₂ | H | H | 1487, 1403, 1213, 1019 |
| 91 | 3-F | H | H | OCH₂ | H | H | 1485, 1271, 1291, 1204 |
| 92 | 3-Cl | H | H | OCH₂ | H | H | 1485, 1227, 1214, 1191 |
| 93 | 3-Br | H | H | OCH₂ | H | H | 1470, 1226, 1213, 1073 |
| 94 | 3-CH₃ | H | H | OCH₂ | H | H | 1487, 1255, 1221, 1205 |
| 95 | H | H | H | OCH₂ | H | CH₃ | 1489, 1406, 1208, 1165 |
| 96 | 3-F | H | H | OCH₂ | H | CH₃ | 1485, 1271, 1231, 1204 |
| 97 | 3-Cl | H | H | OCH₂ | H | CH₃ | 1497, 1472, 1231, 1212 |
| 98 | 3-Br | H | H | OCH₂ | H | CH₃ | 1470, 1424, 1224, 1208 |
| 99 | 3-CH₃ | H | H | OCH₂ | H | CH₃ | 1499, 1403, 1233, 1211 |
| 100 | 3-tert-C₄H₉ | H | H | OCH₂ | H | CH₃ | 1403, 1271, 1235, 1214 |

TABLE 2

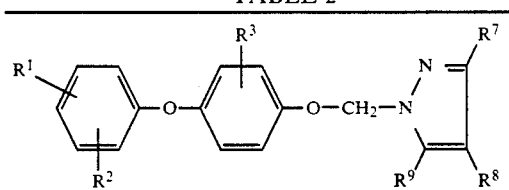

(Ib)

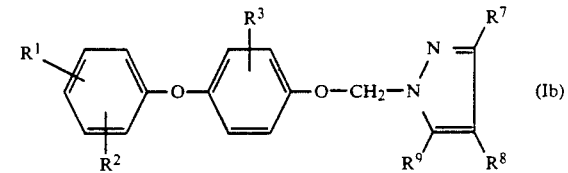

(Ib)

| Compound No. | R¹ | R² | R³ | R⁷ | R⁸ | R⁹ | Phys. data |
|---|---|---|---|---|---|---|---|
| 101 | H | H | H | H | H | H | |
| 102 | 3-F | H | H | H | H | H | |
| 103 | 3-Cl | H | H | H | H | H | |
| 104 | 3-Br | H | H | H | H | H | |
| 105 | 3-CF₃ | H | H | H | H | H | |
| 106 | 3-CH₃ | H | H | H | H | H | |
| 107 | 3-C₂H₅ | H | H | H | H | H | |
| 108 | 3-OCH₃ | H | H | H | H | H | |
| 109 | 3-Cl | 4-F | H | H | H | H | |
| 110 | H | H | H | CH₃ | H | H | |
| 111 | 3-F | H | H | CH₃ | H | H | |
| 112 | 3-Cl | H | H | CH₃ | H | H | |
| 113 | 3-Br | H | H | CH₃ | H | H | |
| 114 | 3-CF₃ | H | H | CH₃ | H | H | |
| 115 | 3-CH₃ | H | H | CH₃ | H | H | |
| 116 | 3-C₂H₅ | H | H | CH₃ | H | H | |
| 117 | 3-OCH₃ | H | H | CH₃ | H | H | |
| 118 | 3-Cl | 4-F | H | CH₃ | H | H | |
| 119 | H | H | H | CH₃ | H | CH₃ | 300 MHz-¹H-NMR in CDCl₃ [ppm]: 5.81 (s) |
| 120 | 3-F | H | H | CH₃ | H | CH₃ | |
| 121 | 3-Cl | H | H | CH₃ | H | CH₃ | |
| 122 | 3-Br | H | H | CH₃ | H | CH₃ | |
| 123 | 3-CF₃ | H | H | CH₃ | H | CH₃ | |
| 124 | 3-CH₃ | H | H | CH₃ | H | CH₃ | |
| 125 | 3-C₂H₅ | H | H | CH₃ | H | CH₃ | |
| 126 | 3-OCH₃ | H | H | CH₃ | H | CH₃ | |
| 127 | 3-Cl | 4-F | H | CH₃ | H | CH₃ | |

TABLE 3

Structure (Ic): R¹-substituted phenyl-O-phenyl(R³)-O-CH₂-N-N=CR¹⁰/N=CR¹¹ (triazine)

| Compound No. | R¹ | R² | R³ | R¹⁰ | R¹¹ | Phys. data |
|---|---|---|---|---|---|---|
| 128 | H | H | H | H | H | mp.: 66–67° C. |
| 129 | H | H | 3-F | H | H | |
| 130 | H | H | 3-Cl | H | H | |
| 131 | 3-F | H | H | H | H | mp.: 39–41° C. |
| 132 | 3-Cl | H | H | H | H | IR absorptions (cm⁻¹): 1502, 1472, 1274, 1232 |
| 133 | 3-Br | H | H | H | H | IR absorptions (cm⁻¹): 1502, 1469, 1273, 1230, 1207 |
| 134 | 3-CF₃ | H | H | H | H | IR absorptions (cm⁻¹): 1503, 1450, 1329, 1276 |
| 135 | 3-CH₃ | H | H | H | H | mp.: 52–54° C. |
| 136 | 3-C₂H₅ | H | H | H | H | mp.: 39–41° C. |
| 137 | 3-tert.-butyl | H | H | H | H | IR absorptions (cm⁻¹): 1502, 1487, 1430, 1273, 1231 |
| 138 | 3-OCH₃ | H | H | H | H | IR absorptions (cm⁻¹): 1502, 1489, 1274, 1223, 1206 |
| 139 | 3-F | 4-F | H | H | H | mp.: 68–70° C. |
| 140 | 3-Cl | 4-F | H | H | H | mp.: 74–75° C. |
| 141 | H | H | 3-F | H | H | |
| 142 | H | H | 3-Cl | H | H | |
| 143 | 3-F | H | 3-Cl | H | H | |
| 144 | 3-F | H | 3-F | H | H | |
| 145 | 3-Cl | H | 3-F | H | H | |
| 146 | 3-Cl | H | 3-Cl | H | H | IR absorptions (cm⁻¹): 1586, 1508, 1491, 1473, 1274 |
| 147 | 3-Br | H | 3-F | H | H | |
| 148 | 3-Br | H | 3-Cl | H | H | IR absorptions (cm⁻¹): 1583, 1490, 1470, 1273, 1260 |
| 149 | 3-CF₃ | H | 3-F | H | H | |
| 150 | 3-CF₃ | H | 3-Cl | H | H | IR absorptions (cm⁻¹): 1509, 1491, 1451, 1329, 1275 |
| 151 | 3-CH₃ | H | 3-F | H | H | |
| 152 | 3-CH₃ | H | 3-Cl | H | H | |
| 153 | 3-C₂H₅ | H | 3-F | H | H | |
| 154 | 3-C₂H₅ | H | 3-Cl | H | H | |
| 155 | 3-OCH₃ | H | 3-F | H | H | |
| 156 | 3-OCH₃ | H | 3-Cl | H | H | |
| 157 | 3-Cl | 4-F | 3-F | H | H | |
| 158 | 3-Cl | 4-F | 3-Cl | H | H | |
| 159 | H | H | H | CH₃ | CH₃ | |
| 160 | 3-F | H | H | CH₃ | CH₃ | |
| 161 | 3-Cl | H | H | CH₃ | CH₃ | |
| 162 | 3-Br | H | H | CH₃ | CH₃ | |
| 163 | 3-CF₃ | H | H | CH₃ | CH₃ | |
| 164 | 3-CH₃ | H | H | CH₃ | CH₃ | |
| 165 | 3-C₂H₅ | H | H | CH₃ | CH₃ | |
| 166 | 3-OCH₃ | H | H | CH₃ | CH₃ | |
| 167 | 3-Cl | 4-F | H | CH₃ | CH₃ | |

TABLE 4

Structure (Id)

| Compound No. | R¹ | R² | R³ | R¹² | R¹³ | Phys. data |
|---|---|---|---|---|---|---|
| 168 | H | H | H | H | H | |
| 169 | 3-F | H | H | H | H | |
| 170 | 3-Cl | H | H | H | H | |
| 171 | 3-Br | H | H | H | H | |
| 172 | 3-CF₃ | H | H | H | H | |
| 173 | 3-CH₃ | H | H | H | H | |
| 174 | 3-C₂H₅ | H | H | H | H | |
| 175 | 3-OCH₃ | H | H | H | H | |
| 176 | 3-Cl | 4-F | H | H | H | |
| 177 | H | H | H | H | Cl | 300 MHz-¹H-NMR in CDCl₃ [ppm]: 5.95 (s) |
| 178 | 3-F | H | H | H | Cl | |
| 179 | 3-Cl | H | H | H | Cl | |
| 180 | 3-Br | H | H | H | Cl | 300 MHz-¹H-NMR in CDCl₃ [ppm]: 8.21 (s) |
| 181 | 3-CF₃ | H | H | H | Cl | 300 MHz-¹H-NMR in CDCl₃ [ppm]: 5.97 (s) |
| 182 | 3-CH₃ | H | H | H | Cl | mp.: 59–62° C. |
| 183 | 3-C₂H₅ | H | H | H | Cl | |
| 184 | 3-OCH₃ | H | H | H | Cl | |
| 185 | 3-Cl | 4-F | H | H | Cl | |
| 186 | H | H | H | CH₃ | CH₃ | |
| 187 | 3-F | H | H | CH₃ | CH₃ | |
| 188 | 3-Cl | H | H | CH₃ | CH₃ | |
| 189 | 3-Br | H | H | CH₃ | CH₃ | |
| 190 | 3-CF₃ | H | H | CH₃ | CH₃ | |
| 191 | 3-CH₃ | H | H | CH₃ | CH₃ | |
| 192 | 3-C₂H₅ | H | H | CH₃ | CH₃ | |
| 193 | 3-OCH₃ | H | H | CH₃ | CH₃ | |

TABLE 4-continued

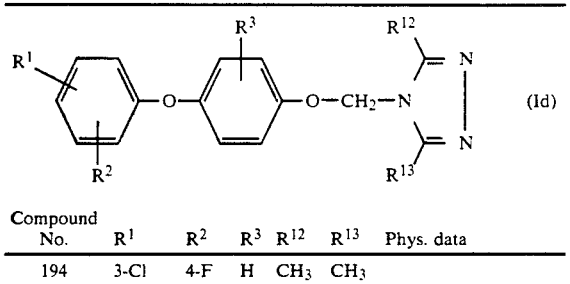

(Id)

| Compound No. | R¹ | R² | R³ | R¹² | R¹³ | Phys. data |
|---|---|---|---|---|---|---|
| 194 | 3-Cl | 4-F | H | CH₃ | CH₃ | |

TABLE 5

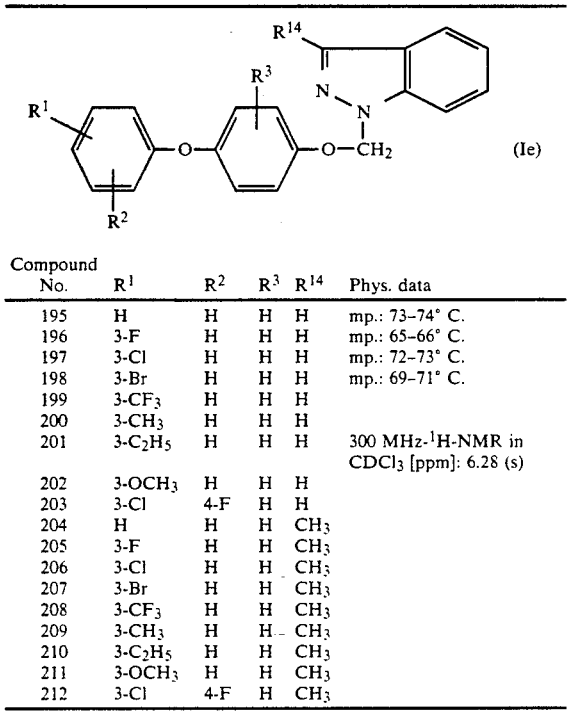

(Ie)

| Compound No. | R¹ | R² | R³ | R¹⁴ | Phys. data |
|---|---|---|---|---|---|
| 195 | H | H | H | H | mp.: 73–74° C. |
| 196 | 3-F | H | H | H | mp.: 65–66° C. |
| 197 | 3-Cl | H | H | H | mp.: 72–73° C. |
| 198 | 3-Br | H | H | H | mp.: 69–71° C. |
| 199 | 3-CF₃ | H | H | H | |
| 200 | 3-CH₃ | H | H | H | |
| 201 | 3-C₂H₅ | H | H | H | 300 MHz-¹H-NMR in CDCl₃ [ppm]: 6.28 (s) |
| 202 | 3-OCH₃ | H | H | H | |
| 203 | 3-Cl | 4-F | H | H | |
| 204 | H | H | H | CH₃ | |
| 205 | 3-F | H | H | CH₃ | |
| 206 | 3-Cl | H | H | CH₃ | |
| 207 | 3-Br | H | H | CH₃ | |
| 208 | 3-CF₃ | H | H | CH₃ | |
| 209 | 3-CH₃ | H | H | CH₃ | |
| 210 | 3-C₂H₅ | H | H | CH₃ | |
| 211 | 3-OCH₃ | H | H | CH₃ | |
| 212 | 3-Cl | 4-F | H | CH₃ | |

TABLE 6

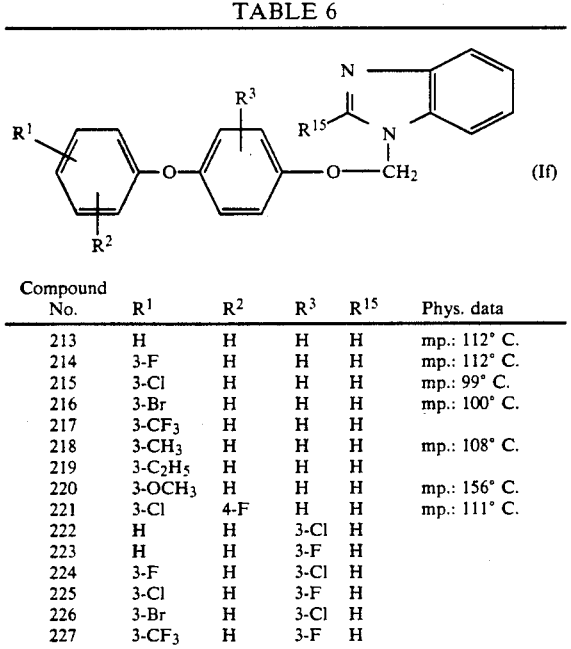

(If)

| Compound No. | R¹ | R² | R³ | R¹⁵ | Phys. data |
|---|---|---|---|---|---|
| 213 | H | H | H | H | mp.: 112° C. |
| 214 | 3-F | H | H | H | mp.: 112° C. |
| 215 | 3-Cl | H | H | H | mp.: 99° C. |
| 216 | 3-Br | H | H | H | mp.: 100° C. |
| 217 | 3-CF₃ | H | H | H | |
| 218 | 3-CH₃ | H | H | H | mp.: 108° C. |
| 219 | 3-C₂H₅ | H | H | H | |
| 220 | 3-OCH₃ | H | H | H | mp.: 156° C. |
| 221 | 3-Cl | 4-F | H | H | mp.: 111° C. |
| 222 | H | H | 3-Cl | H | |
| 223 | H | H | 3-F | H | |
| 224 | 3-F | H | 3-Cl | H | |
| 225 | 3-Cl | H | 3-F | H | |
| 226 | 3-Br | H | 3-Cl | H | |
| 227 | 3-CF₃ | H | 3-F | H | |

TABLE 6-continued

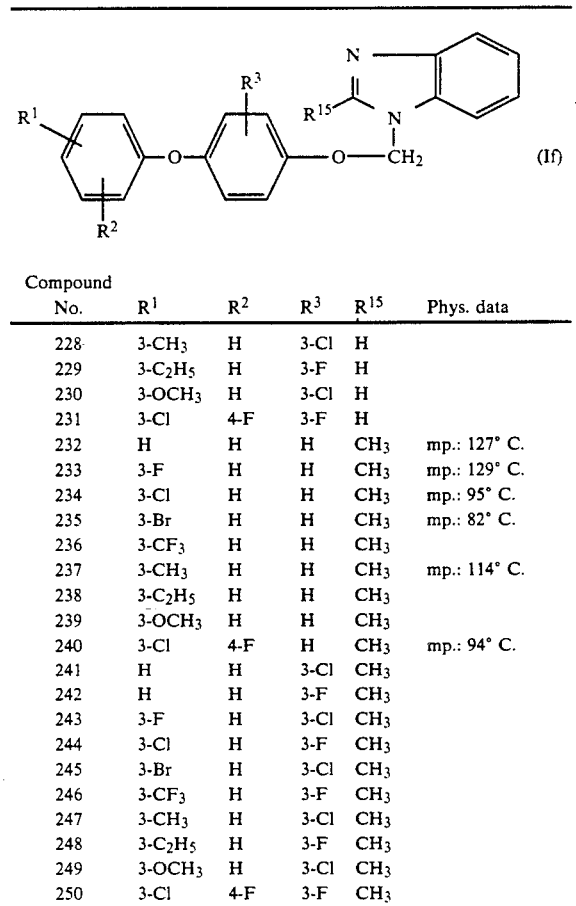

(If)

| Compound No. | R¹ | R² | R³ | R¹⁵ | Phys. data |
|---|---|---|---|---|---|
| 228 | 3-CH₃ | H | 3-Cl | H | |
| 229 | 3-C₂H₅ | H | 3-F | H | |
| 230 | 3-OCH₃ | H | 3-Cl | H | |
| 231 | 3-Cl | 4-F | 3-F | H | |
| 232 | H | H | H | CH₃ | mp.: 127° C. |
| 233 | 3-F | H | H | CH₃ | mp.: 129° C. |
| 234 | 3-Cl | H | H | CH₃ | mp.: 95° C. |
| 235 | 3-Br | H | H | CH₃ | mp.: 82° C. |
| 236 | 3-CF₃ | H | H | CH₃ | |
| 237 | 3-CH₃ | H | H | CH₃ | mp.: 114° C. |
| 238 | 3-C₂H₅ | H | H | CH₃ | |
| 239 | 3-OCH₃ | H | H | CH₃ | |
| 240 | 3-Cl | 4-F | H | CH₃ | mp.: 94° C. |
| 241 | H | H | 3-Cl | CH₃ | |
| 242 | H | H | 3-F | CH₃ | |
| 243 | 3-F | H | 3-Cl | CH₃ | |
| 244 | 3-Cl | H | 3-F | CH₃ | |
| 245 | 3-Br | H | 3-Cl | CH₃ | |
| 246 | 3-CF₃ | H | 3-F | CH₃ | |
| 247 | 3-CH₃ | H | 3-Cl | CH₃ | |
| 248 | 3-C₂H₅ | H | 3-F | CH₃ | |
| 249 | 3-OCH₃ | H | 3-Cl | CH₃ | |
| 250 | 3-Cl | 4-F | 3-F | CH₃ | |

USE EXAMPLES

In the examples below, the action of the compounds according to the invention, or agents containing them, on pests was compared with that of the following prior art compounds:

A: 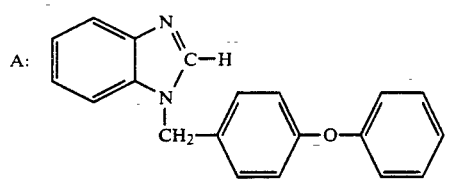

disclosed in EP-A-132 606 as compound no. 1

B: 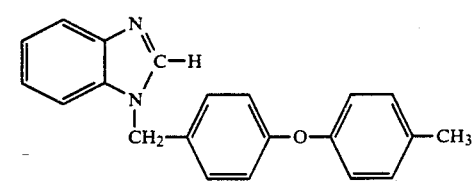

disclosed in EP-A-132 606 as compound no. 8

C: 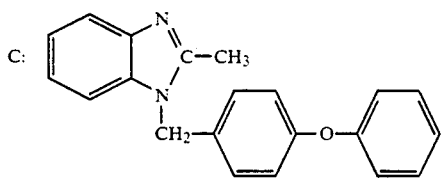

disclosed in
EP-A-132 606 as
compound no. 29

The concentrations at which the investigated compounds achieve a 100% kill or inhibition are the minimum concentrations. At least one replicate was used for each concentration.

Example A

*Dysdercus intermedius* (Cotton Stainer); Breeding Experiment 200 g of sterile quartz sand (particle size: 0-3 mm) was introduced into 1 liter jars. 20 ml of aqueous formulations of the active ingredients was poured onto this sand prior to commencement of the experiment. 10 larvae of the fourth larval stage were then placed in the jars. The food proffered was swollen cotton seeds, which were replaced weekly. The sand was moistened, also weekly, with pure water. The temperature was kept at 25° to 27° C. The observation period extended up to pupation of the adults. The sample was considered to be effective when, on completion of the experiment, the animals were either dead or in the form of giant larvae or intermediate types (adultoids), or exhibited extensive morphological defects.

In this experiment, a 100% kill rate was achieved with $\leq$ 10 ppm of active ingredients 128, 131, 132, 134 and 177. Comparative agents A, B and C had no effect at a rate of 10 ppm.

Example B

*Prodenia litura*; Ovicidal Action

Eggs of *Prodenia litura* laid on parchment and which were not older than 24 hours were cut from the paper. 0.5 ml of aqueous formulations of the active ingredients was then pipetted onto the eggs. The eggs were then placed in plastic pallets lined with filter paper. The pallets were then covered with a glass plate. Assessment took place after about 5 days, when the larvae in the control had emerged.

In this experiment, a quantitative inhibition of hatching was achieved with $\leq$ 0.5 wt % of compounds 128, 131, 132, 136, 150 and 232.

Example C

*Prodenia litura*; Breeding Experiment

Breeding took place in 100 ml plastic breakers containing about 50 ml of the standard nutrient medium with which the active ingredients had been carefully mixed while warm. For each concentration, 1 beaker with 5 caterpillars of the fourth larval stage was employed. The temperature was kept at 25° to 26° C. The experiment was monitored until the moths hatched. The sample was considered to be effective when giant larvae were produced.

In this experiment, a quantitative action was achieved with $\leq$ 0.5 ppm of active ingredients 132 and 134. Comparative agents A, B and C had no effect at a rate of 5.0 ppm.

Example D

Ovicidal Action on *Dysdercus intermedius* (Cotton Stainer)

Pieces of adhesive tape (about 0.8 cm) were stuck to the top edge of plastic plant markers. 24 hours before commencement of the experiment, eggs of the cotton stainer contained in a vessel were attached to the adhesive strips by dipping the markers into the vessel. The eggs were then dipped for 5 seconds into aqueous formulations of the active ingredients and excess liquid was allowed to drip off onto filter paper, care being taken to prevent the eggs coming into contact with the paper. The markers were then placed in plastic trays (adhesive strip at the top). Half a roll of absorbent cotton was moistened with water and placed in each beaker to prevent drying out, and the trays were covered with a glass plate. Assessment took place after the control bugs hatched (after about 8 days).

In this experiment, hatching was inhibited most successfully with 0.005 wt % of compounds 128, 131, 132, 133 and 139. Comparative agents A, B and C had no effect at 0.1 wt %.

Example E

Breeding Experiment with *Aedes aegypti* (Yellow-fever Mosquito)

At 25° C., 200 ml of tapwater containing the active ingredient was filled into 250 ml plastic beakers; 20 to 30 mosquito larvae in the third to fourth larval stage were then introduced. During the experiment, a powdered commercial tropical fishfood was fed once. Pupation and hatching of the imagoes, which took place after about 10 to 12 days, were assessed.

In this experiment, the lethal dose of compound 7 was 0.5 ppm, and that of compound 9 and comparative agents A and C 5 ppm.

We claim:

1. N-substituted azole of the formula I

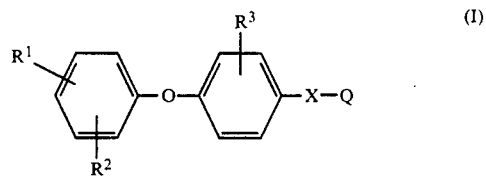

where
$R^1$, $R^2$, $R^3$ are each hydrogen, halogen, $C_1$-$C_8$-alkyl, $C_1$-$C_8$-alkoxy, $C_1$-$C_4$-haloalkyl, $C_1$-$C_4$-haloalkoxy, $C_3$-$C_{10}$-cycloalkyl, nitro or cyano, Q is an unsubstituted or substituted azole group of the formulae

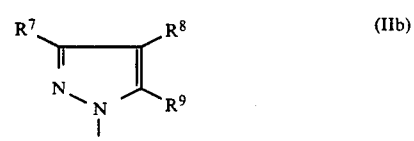

$R^7$ to $R^9$ denoting hydrogen, halogen, $C_1$-$C_8$-alkyl, $C_1$-$C_4$-haloalkyl, $C_1$-$C_4$-alkoxy, $C_3$-$C_{10}$-cycloalkyl or phenyl or naphthyl which is unsubstituted or mono-, di- or trisubstituted by halogen, $C_1$–$C_8$-alkyl, $C_1$–$C_8$-alkoxy, $C_1$–$C_4$-haloalkyl or $C_1$–$C_4$-haloalkoxy, and X is —$OCH_2$—.

2. A composition for combating insects, mites and nematodes containing an N-substituted azole as set forth in claim 1, together with conventional carriers.

3. A composition for combating insects, mites and nematodes as set forth in claim 2, containing from 0.1 to 95 wt % of an N-substituted azole of the formula I.

4. A process for combating insects, arachnids and nematodes, wherein the insects, arachnids and nematodes, or the areas or spaces to be kept free from insects, arachnids and nematodes are treated with a pesticidally effective amount of an N-substituted azole of the formula I as set forth in claim 1.

* * * * *

UNITED STATES PATENT AND TRADEMARK OFFICE
CERTIFICATE OF CORRECTION

PATENT NO. : 5,185,359

DATED : February 9, 1993

INVENTOR(S) : Rainer Buerstinghaus et al.

It is certified that error appears in the above-identified patent and that said Letters Patent is hereby corrected as shown below:

On the title page, Item [54] and column 1, lines 2-4,

The title is incorrect, should read as follows:

--N-PHENOXYPHENYLOXYMETHYL SUBSTITUTED AZOLES AND METHOD FOR CONTROLLING

PESTS THEREWITH--

Signed and Sealed this

Second Day of November, 1993

*Attest:*

BRUCE LEHMAN

*Attesting Officer*         Commissioner of Patents and Trademarks